(12) United States Patent
Boccara et al.

(10) Patent No.: US 10,222,319 B2
(45) Date of Patent: Mar. 5, 2019

(54) METHOD AND DEVICE FOR OPTICALLY DETECTING NANOPARTICLES IN A FLUID SAMPLE

(71) Applicant: ECOLE SUPÉRIEURE DE PHYSIQUE ET DE CHIMIE INDUSTRIELLES DE LA VILLE DE PARIS—ESPCI PARISTECH, Paris (FR)

(72) Inventors: Albert Claude Boccara, Paris (FR); Martine Boccara, Paris (FR)

(73) Assignees: ECOLE SUPÉRIEURE DE PHYSIQUE ET DE CHIMIE INDUSTRIELLES DE LA VILLE DE PARIS, Paris (FR); CENTRE NATIONAL DE LA RECHERCHE SCIENTIFIQUE, Paris (FR); UNIVERSITÉ DE PIERRE ET MARIE CURIE, Paris (FR); ECOLE NORMALE SUPÉRIEURE, Paris (FR); INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 0 days.

(21) Appl. No.: 15/517,723

(22) PCT Filed: Sep. 29, 2015

(86) PCT No.: PCT/EP2015/072425
§ 371 (c)(1),
(2) Date: Apr. 7, 2017

(87) PCT Pub. No.: WO2016/055306
PCT Pub. Date: Apr. 14, 2016

(65) Prior Publication Data
US 2017/0307509 A1    Oct. 26, 2017

(30) Foreign Application Priority Data

Oct. 9, 2014 (FR) ..................... 14 59690

(51) Int. Cl.
*G06K 9/00* (2006.01)
*G01N 15/14* (2006.01)
(Continued)

(52) U.S. Cl.
CPC ..... *G01N 15/1463* (2013.01); *G01N 15/1434* (2013.01); *G01N 15/1459* (2013.01);
(Continued)

(58) Field of Classification Search
None
See application file for complete search history.

(56) References Cited

U.S. PATENT DOCUMENTS

| 2007/0030492 A1* | 2/2007 | Novotny | B82Y 35/00 356/498 |
| 2009/0290156 A1* | 11/2009 | Popescu | G01N 15/1434 356/338 |
| 2017/0307509 A1* | 10/2017 | Boccara | G01N 15/1463 |

FOREIGN PATENT DOCUMENTS

| WO | 2007/100785 A2 | 9/2007 |
| WO | 2012/035170 A1 | 3/2012 |

OTHER PUBLICATIONS

International Search Report issued in PCT/EP2015/072425 dated Feb. 16, 2016 (6 pages).
(Continued)

*Primary Examiner* — Tahmina Ansari
(74) *Attorney, Agent, or Firm* — Osha Liang LLP

(57) ABSTRACT

A device for optically detecting in transmission nanoparticles moving in a fluid sample includes a light source for emitting a spatially incoherent beam for illuminating the sample; an imaging optical system; and a two-dimensional
(Continued)

optical detector. The imaging optical system includes a microscope objective. The two-dimensional optical detector includes a detection plane conjugated with an object focal plane of the microscope objective by said imaging optical system. The two-dimensional optical detector allows a sequence of images of an analysis volume of the sample to be acquired, each image resulting from optical interferences between the illuminating beam incident on the sample and the beams scattered by each of the nanoparticles present in the analysis volume during a preset duration shorter than one millisecond. The device further includes an image processor that allows an average of a sequence of said images to be taken and said average to be subtracted from each image in order to determine, for each nanoparticle of the analysis volume, the amplitude of the scattered beam.

8 Claims, 7 Drawing Sheets

(51) Int. Cl.
*G01N 21/45* (2006.01)
*G02B 21/00* (2006.01)
*G06T 7/00* (2017.01)
*G02B 21/14* (2006.01)
*G02B 21/36* (2006.01)
*G01N 21/47* (2006.01)
*G01N 15/00* (2006.01)

(52) U.S. Cl.
CPC ......... *G01N 21/45* (2013.01); *G02B 21/0056* (2013.01); *G02B 21/14* (2013.01); *G02B 21/367* (2013.01); *G06T 7/0012* (2013.01); *G01N 21/4788* (2013.01); *G01N 2015/0038* (2013.01); *G01N 2015/144* (2013.01); *G01N 2015/1488* (2013.01); *G06T 2207/10056* (2013.01)

(56) References Cited

OTHER PUBLICATIONS

Written Opinion of the International Searching Authority issued in PCT/EP2015/072425 dated Feb. 16, 2016 (6 pages).
Børsheim, K.Y. et al.; "Enumeration and Biomass Estimation of Planktonic Bacteria and Viruses by Transmission Electron Microscopy"; Applied and Environmental Microbiology, vol. 56, No. 2, Feb. 1990, pp. 352-356 (5 pages).
Bettarel et al.; "A Comparison of Methods for Counting Viruses in Aquatic Systems"; Applied and Environmental Microbiology, vol. 66, No. 6, Jun. 2000, pp. 2283-2289 (7 pages).
Balch, W.M. et al.; "Light scattering by viral suspensions"; Limnology Oceanography, vol. 45, Issue 2, 2000, pp. 492-498 (7 pages).
Mitra et al.; "Real-time Optical Detection of Single Human and Bacterial Viruses Based on Dark-field Interferometry"; Biosens Bioelectron., vol. 31, No. 1, Jan. 15, 2012, pp. 499-504 (15 pages).

* cited by examiner

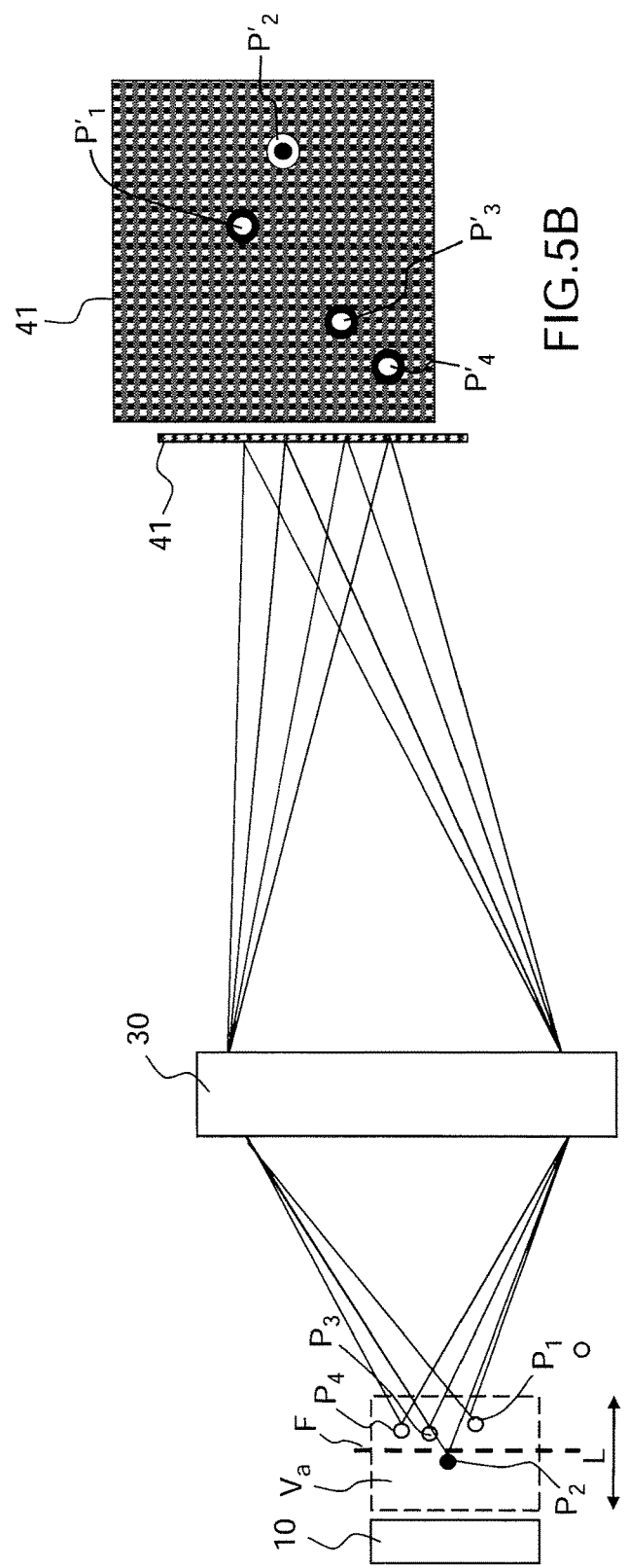

METHOD AND DEVICE FOR OPTICALLY DETECTING NANOPARTICLES IN A FLUID SAMPLE

PRIOR ART

Technical Field of the Invention

The present invention concerns a method and a device for optical detection of nanoparticles in a fluid sample, such as a liquid sample, or in air, typically for nanoparticles of 30 nm to 200 nm. The method applies more particularly to the detection of free virus present in an aquatic environment, especially for the counting and the characterization of virus in seawater or in river water.

Prior Art

Viruses are nano-objects whose dimensions are typically between 30 nm and 200 nm. They are generally specific to a given host cell and thus they are characteristic of a species, or even a variety or strain of that species. Only since 1989, thanks to the work of a Norwegian team (see K. J. Børsheim et al. "Enumeration and biomass estimation of planktonic bacteria and viruses by transmission electron microscopy", Appl. Environ. Microbiol. (1990) 56: 352-356) have we become aware of the abundance of viruses in various aquatic environments. High concentrations of them have been measured in lakes, rivers, ice or sediments of ocean depths, sometimes even in the clouds, which suggests that they play an important role in the functioning of the biosphere. Thanks to various mechanisms, such as the destruction of a dominant species to the benefit of more rare species or the transfer of viral genes to the host, viruses maintain the biodiversity of aquatic ecosystems and facilitate genetic mixing. Thus, it is critical to characterize viruses in the different aquatic ecosystems and to estimate their distribution in order to better understand the relations between viruses and the host.

Depending on the aquatic ecosystems, the season, or even the depth of sampling, the concentrations of free virus generally range between $10^6$ and $10^9$ particles per milliliter. There are many known methods for the characterization and the counting of viruses in aquatic mediums.

For example, we know of transmission electron microscopy (or TEM), which allows us to count the viruses and characterize their morphology with a very good precision. However, this destructive technique requires bulky and costly equipment.

Among the optical techniques for characterization of virus in aquatic environments, we know of epifluorescence microscopy which, after staining the nucleic acids with fluorescent markers, makes it possible to count the free viruses (see for example Bettarel et al., "A comparison of Methods for Counting Viruses in Aquatic Systems", Appl Environ Microbiol, 66:2283-2289 (2000)). However, this technique requires a stage of fixation of the markers, which may prove to be troublesome for the later stages of molecular and biochemical analysis.

Due to the fact that viruses behave like dielectric nanometric particles whose index of refraction, close to 1.5 in the visible spectrum, differs significantly from that of water (1.33), it is likewise known how to detect their presence and potentially characterize them by determining the perturbation which these nanoparticles cause in an incident electromagnetic field.

Thus, methods based on the scattering of light by suspensions of viral particles have been described (see, for example, W M Balch et al., "Light scattering by Viral Suspensions", Limnol Oceanogr, 45:492-498 (2000)). However, these methods are limited to analyses of homogeneous solutions of virus due the poor sensitivity of the detection and they are only able to determine the virus concentration for a given size and shape; thus, they are not adapted to the identification of diversified viruses, which is generally the case in a natural environment.

In order to gain sensitivity, interferometric methods have been used for the detection of virus in a liquid environment. Thus, the article of Mitra et al. ("Real-time Optical Detection of Single Human and Bacterial Viruses Based on Dark-field Interferometry", Biosens Bioelectron. 2012 Jan. 15; 31(1): 499-504) describes a method of interferometric detection for the observation of nanoparticles moving one by one in a nanofluidic conduit. The low light intensity scattered by a nanoparticle illuminated by an incident laser beam is amplified by a reference beam of high intensity. Moreover, a structured illumination gets rid of the noise resulting from parasitic reflections on the interfaces of the conduit (detection on a black background). However, this technique requires a complex nanofluidic layout, besides the use of a coherent source (laser).

The present invention presents an interferometric technique for the detection of nanoparticles in movement in a fluid, such as water, which operates in spatially incoherent illumination, avoiding the need for a laser. Furthermore, the technique described does not require a specific layout for the fluid being examined. However, the technique described in the present specification has a very good sensitivity, and makes it possible to detect nanoparticles with diameters as small as several tens of nanometers.

SUMMARY

According to a first aspect, the present description relates to a device for optically detecting in transmission nanoparticles moving in a fluid sample, comprising:
  a light source for emitting a spatially incoherent beam for illuminating the sample;
  an imaging optical system comprising a microscope objective;
  a two-dimensional optical detector comprising a detection plane conjugated with an object focal plane of the microscope objective by said imaging optical system, and allowing a sequence of images of an analysis volume of the sample to be acquired, each image resulting from optical interference between the illuminating beam incident on the sample and the beams scattered by each of the nanoparticles present in the analysis volume during a preset duration shorter than one millisecond;
  image processing means allowing an average of a sequence of said images to be taken and said average to be subtracted from each image in order to determine, for each nanoparticle of the analysis volume, the amplitude of the scattered beam.

The detection device is used for the detection of nanoparticles, that is, particles with diameter less than several hundreds of nanometers, and more particularly nanoparticles whose diameters are between 30 nm and 200 nm.

The device so described, very easy to implement and not requiring that the sample be placed in a particular form, makes possible the detection of nanoparticles with diameters as small as several tens of nanometers, due to the amplification of the scattering signal obtained by interference between the signal emitted by the source and the signal scattered by each of the nanoparticles during very short times when the nanoparticles are "frozen".

The interferences produced directly between the incident illumination beam and the beams scattered by each of the nanoparticles do not require an initial physical separation between a reference wave and a wave illuminating the sample for the formation of the interferences, such as the interferometer making use of a separator.

The illumination by means of a spatially incoherent beam makes it possible to limit the spatial coherence to the level of a "voxel" whose section is inversely proportional to the numerical aperture of the microscope objective. Thus, interferences are only possible within a voxel inside which a nanoparticle is situated; the interferences thus take place between nearly concentric spherical waves.

According to one or more sample embodiments, the light source is a pulsed source, enabling the sequential emitting of light pulses of said preset duration; the device furthermore comprises means of synchronization of the two-dimensional optical detector and the pulsed light source for the acquisition of said sequence of images. The two-dimensional detector used can then be a standard camera operating at a hundred Hz.

Alternatively, one could work with a continuous source and a high speed camera, typically having a frequency greater than several thousands of images per second.

The light source is a spatially incoherent light source, for example a LED, and is able to avoid any speckle effects which might generate a parasitic background in the area of the detection.

According to one or more sample embodiments, the microscope objective used has a numerical aperture greater than or equal to 1, in order to increase the intensity of the light signal scattered by each of the nanoparticles and enable the detection of nanoparticles of smaller diameter.

According to a second aspect, the invention relates to a method for detecting in transmission nanoparticles moving in a fluid sample, comprising:

the emitting of a spatially incoherent beam for illuminating the sample;

the forming, on the detection plane of a two-dimensional optical detector, and by means of an imaging optical system comprising a microscope objective, of images of the analysis volume of the sample located in the vicinity of an object focal plane of the microscope objective;

the acquiring, by means of the two-dimensional detector, of a sequence of images of an analysis volume of the sample, each image resulting from optical interference between the illuminating beam incident on the sample and the beam scattered by each of the nanoparticles present in the analysis volume during a preset duration shorter than one millisecond;

the processing of the images to take an average of a sequence of said images and subtract said average from each image in order to determine, for each nanoparticle of the analysis volume, the amplitude of the scattered beam.

According to one or more sample embodiments, the emission of the light beam is a sequential emission of light pulses of said preset duration, the acquisition of the images being synchronized with the emission of the light pulses.

According to one or more sample embodiments, the method furthermore comprises the determination of the trajectories of the nanoparticles starting from the sequence of images processed in this way.

BRIEF DESCRIPTION OF THE DRAWINGS

Other advantages and characteristics of the invention will appear upon perusal of the description, illustrated by the following figures:

FIG. 5A, a diagram illustrating the principle of interference between the transmitted wave and the wave scattered by each of several nanoparticles situated before or after the object focal plane of the microscope objective and FIG. 5B, the resulting interference pattern in the detection plane of the detector;

For consistency, the same elements are referenced by the same numbers in the different figures.

DETAILED DESCRIPTION

Figure 1:
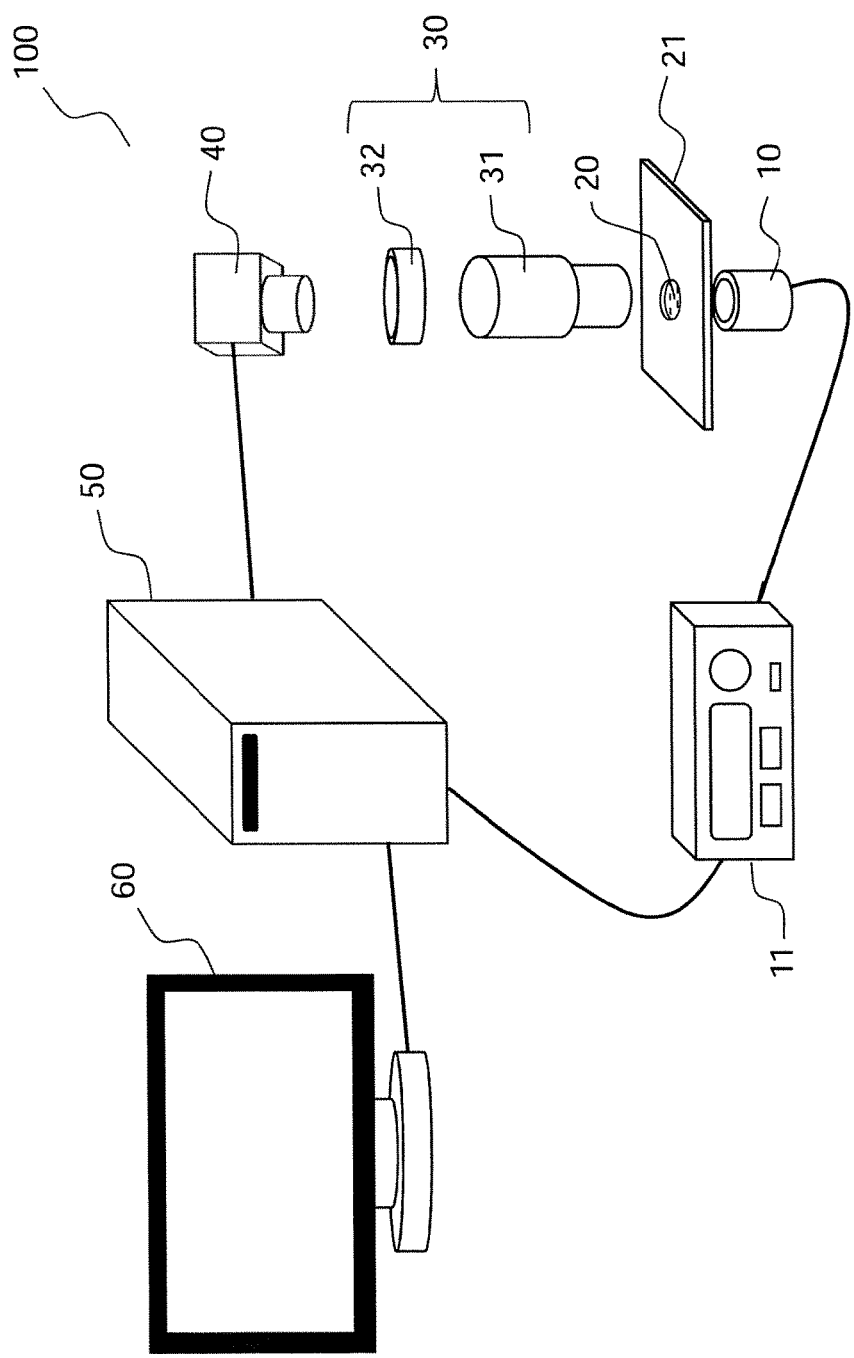
FIG. 1, a diagram illustrating an example of a detection device for nanoparticles in a fluid sample according to the present description.
Figure 2:
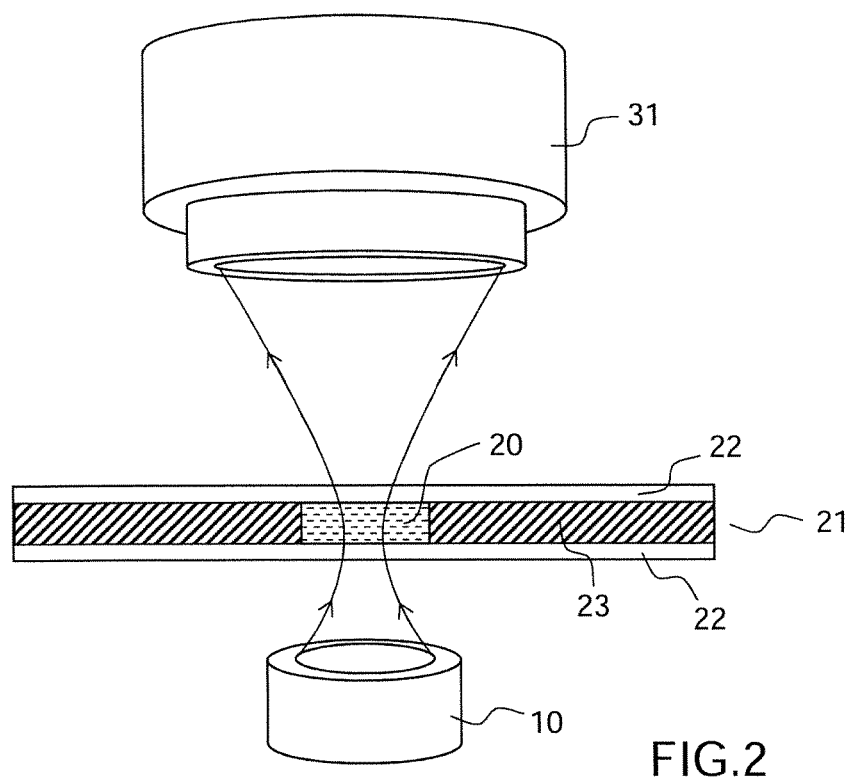
FIG. 2, a diagram showing in greater detail an example of the liquid sample support in a device of the type in FIG. 1.

FIG. 1 shows in schematic fashion an example of a device for detection of nanoparticles in movement in a fluid sample, according to the present description, and FIG. 2 shows a particular example of the arrangement of the sample in a device of the type in FIG. 1.

The detection device 100 shown in FIG. 1 comprises a light source 10 adapted for the emitting of an incident beam through a liquid or gaseous sample 20. The source is a spatially incoherent source, such as a thermal source or a LED (Light-Emitting Diode). The light source 10 illuminates the field of a microscope objective 31 of large numerical aperture, typically greater than 1. The device 100 represented in FIG. 1 furthermore comprises an optics 32, commonly called a tube lens, which together with the microscope objective 31 forms an optical imaging system 30 adapted to form an image of the object focal plane of the microscope objective on a detection plane of a two-dimensional optical detector 40. The objective is for example a standard oil immersion microscope objective and the two-dimensional detector is for example a camera, e.g. CCD or CMOS, typically operating with a minimum rate on the order of a hundred Hz and a large well capacity, for example, on the order of at least a hundred thousand electrons. The well capacity sets the signal to noise ratio and thus the smallest measurable size of virus. In the example of FIG. 1, the detection device 100 furthermore comprises processing means 50 connected to the detector 40 and to a screen 60, as well as, in this example, to a control unit 11 of the light source 10 in order to provide the synchronization between the source when functioning in pulse mode and the detection.

As is shown in greater detail in FIG. 2, the sample 20 is for example a liquid sample whose volume is on the order of a microliter; the volume is formed by a circular hole (with a radius on the order of a millimeter, for example) in a plastic film 23 with thickness roughly equal to a hundred micrometers, placed between 2 microscope coverslips 22, the whole forming a specimen holder 21. No particular preparation is needed for the analysis of the liquid sample, other than occasionally a preliminary filtering to separate the very large particles and keep only the particles with diameter less than a few hundred nanometers, advantageously less than a hundred nanometers, for example; however, in the case of particularly "clean" samples (low concentration of virus), one may have to "concentrate" the virus sample by known methods.

Although described for the case of a liquid sample, the method for detection of nanoparticles according to the present description could also be applied to nanoparticles in movement in a gas, such as air; in this case, the device 100 can be installed directly in the environment whose air is being analyzed. A preliminary filtering could also be done to limit the detection to particles with diameter less than several hundred nanometers.

Figure 3:
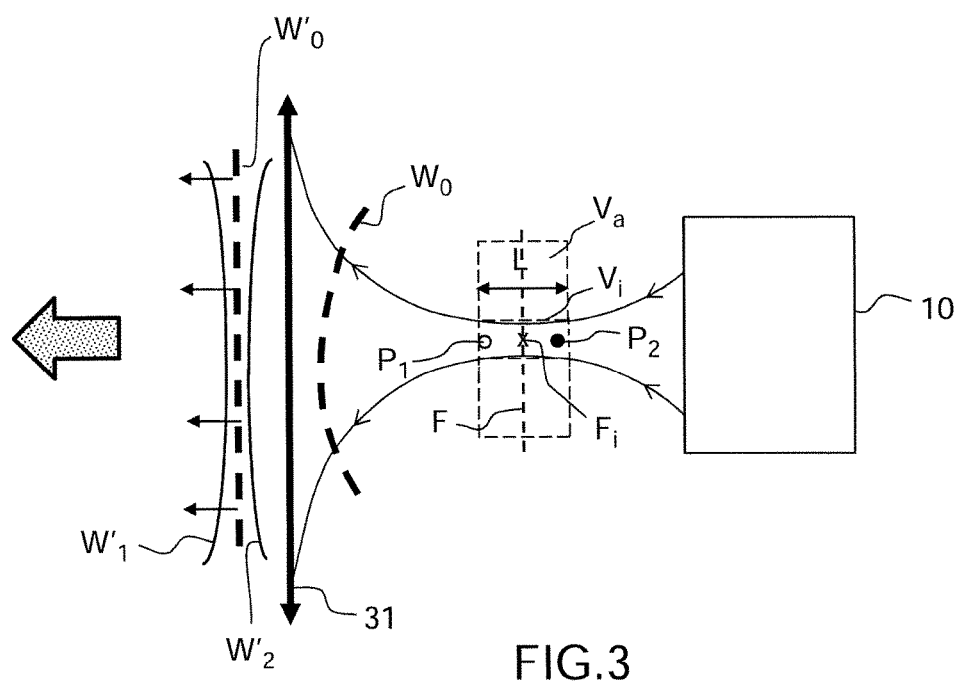
FIG. 3, a diagram illustrating the spherical waves coming from nanoparticles situated before and after the object focal plane of the microscope objective, in an example of the device such as that in FIG. 1.

The principle of the invention is illustrated by means of FIG. 3 for a volume corresponding to one "pixel" of the object field or "voxel"; FIG. 3 shows in schematic manner the spherical waves coming from two nanoparticles situated respectively in the object field before and after the object focal plane of the microscope objective.

By a pixel of the object field or "voxel" is meant an elementary volume $V_i$ defined in the object space of the microscope objective 31 for a pixel of the image field, the image field being defined by the effective detection surface of the detector 40.

A voxel $V_i$ in the object field can be represented by a cylindrical volume of length L defined by the depth of field of the microscope objective 31 and the section S defined by the diffraction spot of the microscope objective. The depth of field L and the diameter $\phi$ of the section S are given by:

$$L = 1,22 \frac{\lambda n}{NA^2} \quad (1)$$

$$\Phi = 1,22 \frac{\lambda}{NA} \quad (2)$$

Where NA is the numerical aperture of the microscope objective, n is the index of the medium of the object space (for example, a medium of index n≈1.5 in the case of an oil immersion microscope objective) and $\lambda$ is the working wavelength of the light wave emitted by the source 10.

One can thus define an analysis volume $V_a$ of the sample by the totality of voxels $V_i$; the analysis volume $V_a$ represents the volume inside which particles in movement in the fluid can be detected. The analysis volume has a lateral dimension defined by the dimension of the object field, that is, the dimension of the detection surface multiplied by the inverse of the magnification of the imaging system 30, and an axial dimension defined by the field depth L.

As shown in FIG. 3, the wave coming from a point $F_i$ of the focal plane F of the microscope objective 31 is a spherical wave $W_0$ of center $F_i$ which the microscope objective transforms into a plane wave $W'_0$. The plane wave $W'_0$, hereinafter called the "reference wave", encounters the microscope tube lens (not shown in FIG. 3). In the detection plane of the detector 40, this plane wave forms a diffraction spot whose diameter is a function of the numerical aperture of the microscope objective and of the magnification of the imaging system 30.

Inside the voxel $V_i$, sub-wavelength nanoparticles $P_1$ and $P_2$, that is, with dimension less than the working wavelength, and situated in the vicinity of the point $F_i$ but at the limits of the field depth, when illuminated by the light wave coming from the source 10 each emit a scattered spherical wave which the microscope objective 31 transforms into a quasi-plane wave, respectively noted as $W'_1$, $W'_2$ in FIG. 3. The nanoparticles are too small to cause a phase shift. On the other hand, the spatial coherence within a voxel in the presence of a nanoparticle generates interferences between the nearly concentric spherical waves coming respectively from the illumination beam and the beam scattered by the nanoparticle.

The method of detection according to the present description is based on the acquisition, by means of the two-dimensional detector 40, of a sequence of images of the analysis volume of the sample, each image resulting from optical interference between the incident beam emitted during a preset duration which is sufficiently short in relation to the time of movement of a nanoparticle, typically less than one millisecond, and the beam scattered by each of the nanoparticles present in the analysis volume formed from the incident beam. Thus, in the example of FIG. 3, each of the waves $W'_1$, $W'_2$ interferes with the reference wave $W'_0$. It can be shown (see below) that depending on whether the nanoparticle is located downstream from the object focal plane of the microscope (for example, the particle $P_1$) or upstream (for example, the particle $P_2$), the interference will be constructive or destructive. This difference is due to the "Gouy phase", which is the cause of the 180° phase shift between a spherical wave coming from a point located before or after the focus.

Figure 4A:
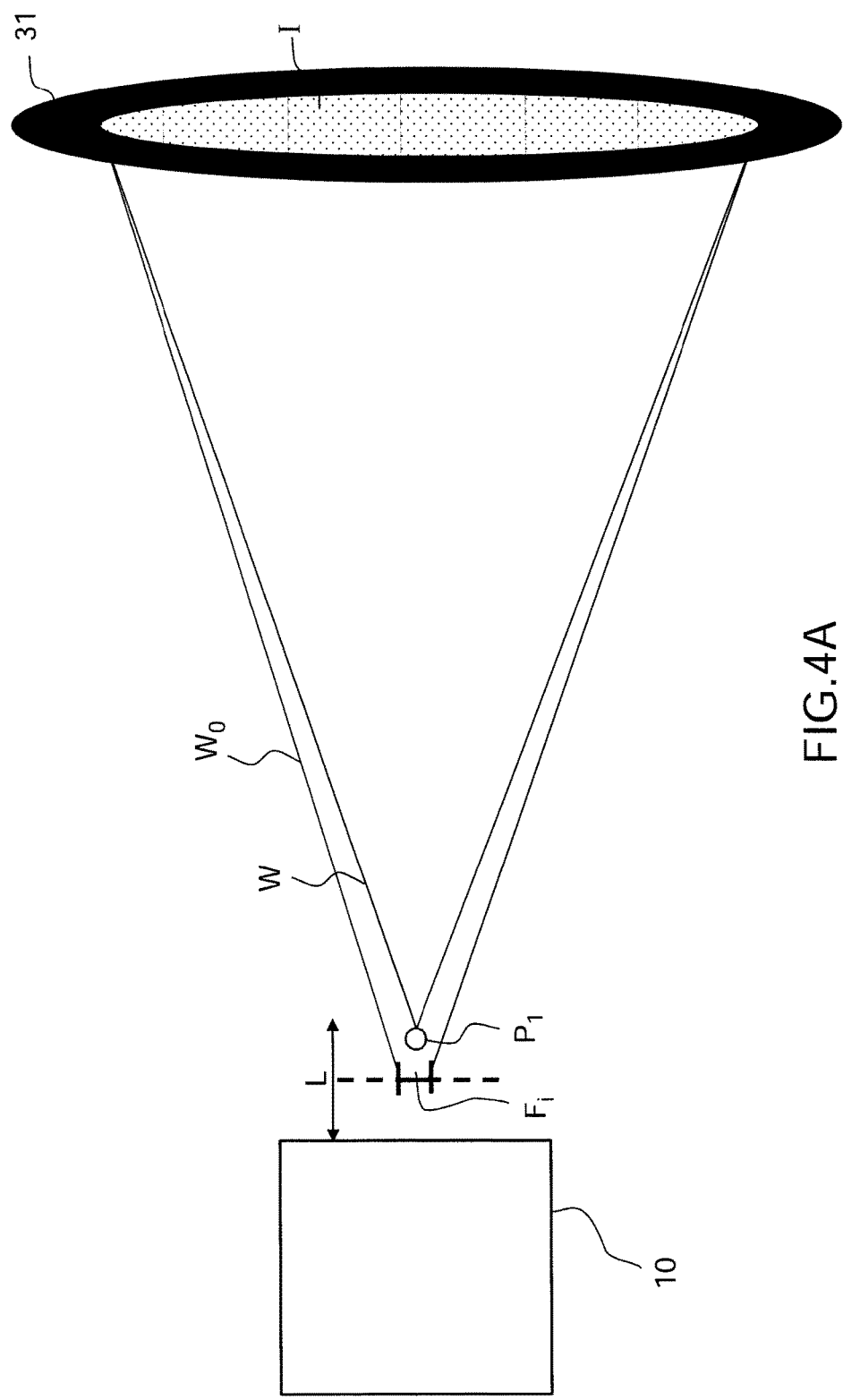
FIGS. 4A and 4B, diagrams illustrating the principle of interference between the transmitted wave and the wave scattered by a nanoparticle, respectively in the case of a particle situated after the object focal plane of the microscope objective and before the object focal plane of the microscope objective.
Figure 4B:
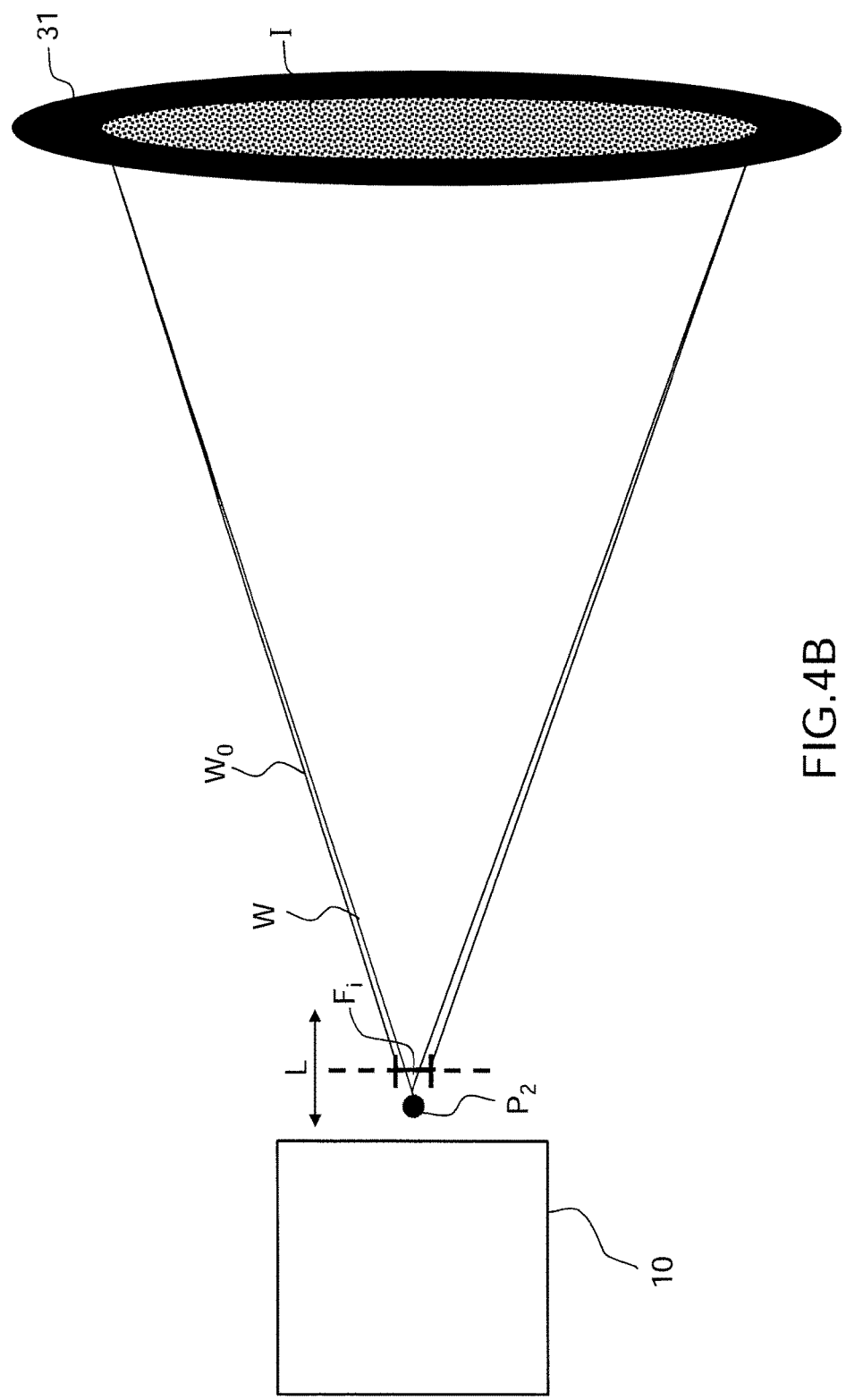

FIGS. 4A and 4B thus illustrate the mechanism of constructive and destructive interference, respectively, for nanoparticles positioned downstream and upstream, respectively, from the object focal plane of the microscope objective, yet always in the field depth. In these figures, only the source 10 and the microscope objective 31 are shown.

The example of FIG. 4A illustrates the case of a nanoparticle $P_1$ situated downstream from the object focal plane of the microscope objective 31. The nanoparticle $P_1$ is situated in the analysis volume defined by the field of the detector (not represented in FIG. 4A) and the field depth L of the microscope objective 31. The nanoparticle is illuminated by the source 10, advantageously a spatially and temporally incoherent source, such as a LED, in order to avoid the formation of speckle which might hinder the interpretation of the interference signals.

We denote here as $W_0$ the reference wave coming from the focal point $F_i$ and intercepted by the aperture of the microscope objective and as W the wave scattered by the nanoparticle $P_1$, likewise intercepted by the aperture of the microscope objective. In the case of FIG. 4A, the reference wave and the scattered wave are spherical waves in phase. Constructive interference is produced between the waves, which translates in the area of the aperture of the microscope objective into a light interference pattern I. The phase shift between the position of the nanoparticle and the focus being less than the field depth, the waves W and $W_0$ are in phase for all angles of rays scattered in the aperture of the microscope objective, that is, all angles formed between the optical axis of the microscope objective and the maximum aperture of the objective, or typically 54° for an oil immersion objective. Hence, one does not see rings in the interference field of FIG. 4A.

The example of FIG. 4B on the other hand illustrates the case of a nanoparticle $P_2$ situated downstream from the object focal plane of the microscope objective 31, yet still in the analysis volume whose width is defined by the field depth of the microscope objective 31. In this example, the reference wave $W_0$ and the scattered wave W are out of phase due to the introduction of the Gouy phase. Destructive interference is produced between the waves, translating in the area of the aperture of the microscope objective into a dark interference pattern I. As previously, the phase shift between the position of the nanoparticle and the focus being less than the field depth, the waves W and $W_0$ are out of phase for all angles and one does not see any rings.

In an interference phenomenon between a very weak signal, such as that scattered by each of the nanoparticles, and the strong signal coming from the source, as is described by means of FIGS. 4A and 4B, one observes an amplification by interference which enables the detecting of very small scattering signals and thus an identification of nanoparticles with diameters less than several tens of nanometers.

Thus, designating as $N_S$ the number of photoelectrons induced directly by the photons of the source and as $N_D$ those produced by the scattering nanoparticle, one obtains by interference between these two waves a number of photoelectrons N such that:

$$N = N_S + N_D + 2\sqrt{N_S N_D} \cos(\Phi) \quad (3)$$

Where $\Phi$ is the phase shift between the source beam and the scattered beam.

Here, the number $N_D$ of photoelectrons produced by the scattering nanoparticle is very small compared to the number $N_S$ of photoelectrons emitted by the source (ratio typically $1/10^6$). Moreover, in our case, due to the position of the particles in the field depth of the microscope objective, the phase shift $\Phi$ is close to zero or 180° depending on the relative position of the scattering particle and the focus; therefore, cos ($\Phi$) is equal to +1 or −1.

Thus, if one takes the average over a large number of images, taking into account the movement of the particles, generally a Brownian movement due to the very small size of the particles, the average taken over all of the images will represent the background ($N_S$), since the signals associated with the particles are reduced to the level of the noise. In order to obtain images containing only the signals associated with the nanoparticles, one can then subtract the average from each image acquired. One then obtains the interference term $2\sqrt{N_S N_D}$, constituting the signal after removal of the background, and being much greater than $N_D$. Based on the measurement of the interference term, one can obtain the amplitude of the beam scattered by the nanoparticle $\sqrt{N_D}$, $N_S$ being known, and deduce from this information such as the size of the particle, the amplitude of the scattered signal varying as the cube of the particle size.

A calculation of the signal to noise ratio with a detector able to store 160,000 electrons per pixel shows that, after processing by subtraction of the average, the residual measurement noise corresponds to the signal which would be created by particles with diameter of 20 nanometers.

Furthermore, the use of a microscope objective of large numerical aperture NA, typically NA equal to or greater than 1, will enable not only an increasing of the solid angle of light collection but also an increasing of the strength of the signal scattered by each nanoparticle and therefore a decreasing of the minimum diameter of observable nanoparticles. In fact, the strength scattered by a nanoparticle varies as σ/S, where σ is the effective scattering cross section of the nanoparticle and S is the surface of the diffraction spot; thus, per equation (2) above, the strength scattered by a nanoparticle varies with the square of the numerical aperture NA.

FIG. 5B shows schematically an image obtained at a given moment for the observation of a plurality of nanoparticles in movement in a fluid medium, such as that represented in FIG. 5A.

FIG. 5A shows 4 nanoparticles referenced as $P_1$ to $P_4$, the nanoparticles $P_1$, $P_3$, $P_4$ being situated downstream from the focal plane of the microscope objective and the particle $P_2$ being situated upstream from the focal plane of the microscope objective. All the particles are located in the analysis volume $V_a$ defined by the field of the detector and the field depth L of the microscope objective.

The nanoparticles are in movement in the fluid medium. For example, they may be nanoparticles of several tens of nanometers to several hundreds of nanometers, such as viruses in aquatic environment. During the implementing of the method of detection according to the present description, one acquires a series of images, each image resulting from optical interference between the incident beam emitted and the beams scattered by each of the nanoparticles during a given sufficiently short time so as to "freeze" the movement of the particles in the analysis volume.

As is known, the scattering ability of a spherical nanoparticle of radius r undergoing Brownian movement is given by the formula:

$$D = k_B T / 6\pi \eta r \quad (4)$$

where $k_B$ is the Boltzmann constant and $\eta$ is the viscosity of the fluid in which the nanoparticle is immersed at temperature T.

For an interval of time t, the jump l of the particle as imaged in 2 dimensions on the camera is given by: $l = \sqrt{4Dt}$ where D is the scattering ability given by equation (4).

Thus, in practice one tries to form images during sufficiently short times t so that the nanoparticle has not covered a distance greater than a fraction of the diffraction spot. Typically, it is shown that the images should be formed during durations not exceeding a millisecond.

According to a first variant, the movement can be frozen by the detection, utilizing a camera having a very high rate of acquisition, typically greater than several thousand images per second.

Alternatively, one can use a pulsed source with duration less than a millisecond, synchronized with the acquisition of each of the images on the detector. In this case, the detector can be a standard camera with an acquisition rate of a hundred Hz, for example. The "jump" experienced by a nanoparticle of several tens of nanometers in radius, such as around 40 nm, and measured between 2 consecutive images, is greater than 1 micrometer, which is easily measurable given the resolution of the microscope objectives used.

As explained above by means of FIGS. 4A and 4B, the nanoparticles located downstream from the focal plane of the microscope objective will give rise to constructive interference, resulting in light diffraction spots ($P'_1$, $P'_3$, $P'_4$) on the detection plane 41 shown in FIG. 5B. On the other hand, the nanoparticles located upstream from the focal plane of the microscope objective will give rise to destructive interference, resulting in dark diffraction spots on the detection plane ($P'_2$).

In practice, as explained above, one observes on the detection plane 41 a substantial background, on which is superimposed diffraction spots which are lighter or darker than the background, depending on whether the interference is constructive or destructive. Advantageously, according to the method of detection of the present description, one records a sequence of images, for example, several hundred, and takes the average of them. To obtain the images only containing the signals associated with the nanoparticles, one can then subtract the average from each image acquired.

Figure 6C:
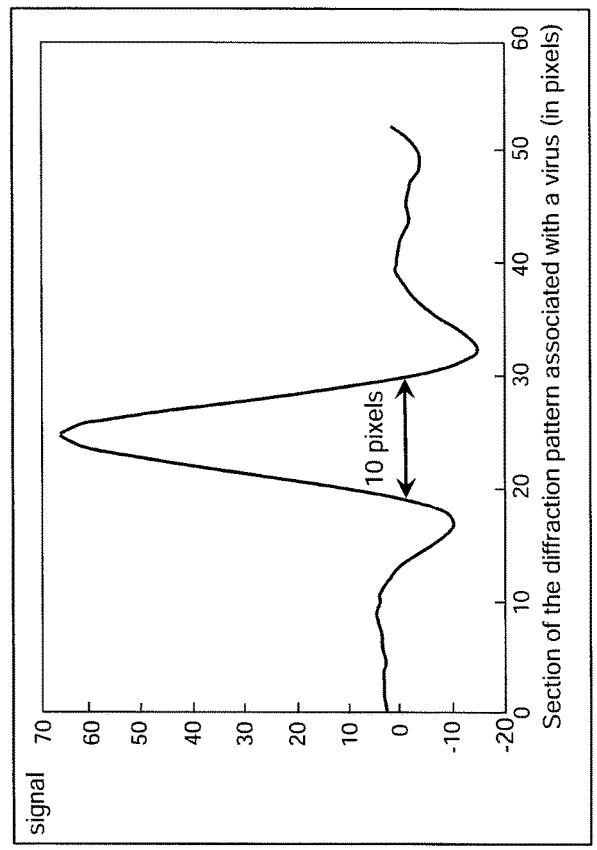
FIGS. 6A to 6C, figures showing respectively an image obtained for a liquid sample after processing by removal of the average, a zoom of an interference pattern of said image associated with a particle corresponding to a virus of "phage $\lambda$" type and a light intensity profile measured in the area of said particle as a function of the number of pixels in the detection plane of the detector.
Figure 6B:
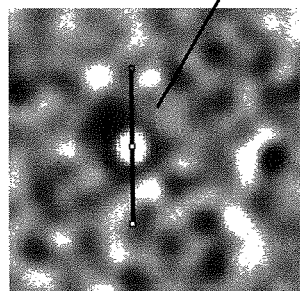
Figure 6A:
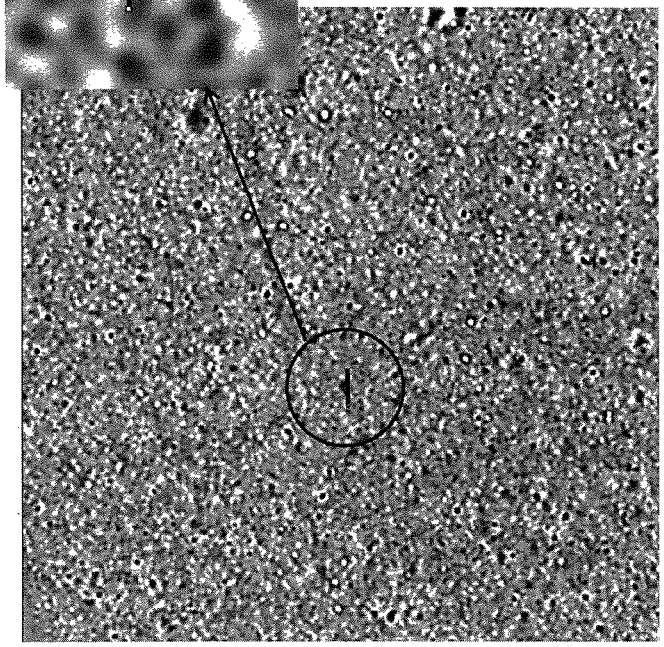
Figure 7:
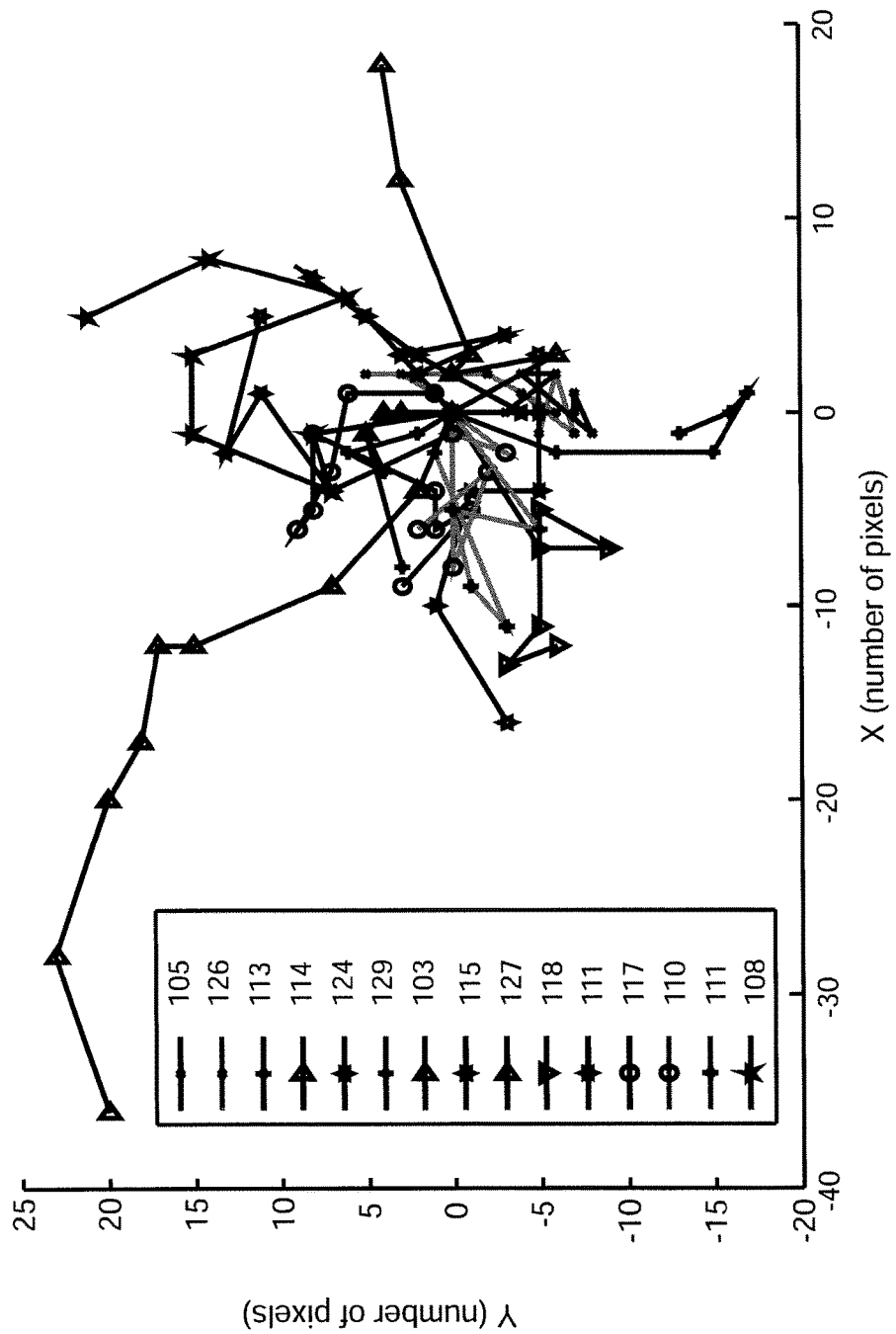
FIG. 7, a curve illustrating the trajectories of different nanoparticles (virus of Phage T4 type), the trajectories being referenced by series of jumps between two consecutive images.

FIGS. 6 and 7 show the first experimental results obtained with liquid samples analyzed by using the method of detection according to the present description to detect and identify viruses which are potentially present. This concerns, respectively, a sample containing viruses of phage λ, type and a sample containing viruses of phage T4 type, a sample very representative of what one finds on the coast of Brittany.

FIG. 6A is an image obtained from a liquid sample after processing by removal of the average. The device used to obtain this image is a device of the kind shown in FIG. 1 with a Thorlabs® Imperial blue LED, an oil immersion objective Olympus® 100X, a tube lens of 300 mm focus for over-sampling the diffraction spot and a CMOS Photon Focus® PHF-MV-D1024E-160-CL-12 camera. One observes in FIG. 6A a group of light or dark spots, each one corresponding to a nanoparticle situated upstream or downstream from the object focal plane of the microscope objective.

FIG. 6B shows a zoom of an interference pattern of the image of FIG. 6A associated with an isolated nanoparticle and FIG. 6C illustrates the light intensity profile (in units calibrated with the aid of nanoparticles of known size) measured in the area of said particle as a function of the number of pixels in the detection plane of the detector and corresponding to the amplitude of the beam scattered by the nanoparticle.

It is possible, with the obtained images, not only to confirm the presence of viruses but also to identify them, in particular, as a function of their size; in the present case, the measurement of the scattered light intensity makes it possible to infer a nanoparticle with diameter of 60 nm, corresponding to the "phage λ" virus.

FIG. 7 illustrates the trajectories of a certain number of particles measured during a period on the order of a tenth of a second, with a device similar to the one used to form the images shown in FIG. 6A. Each trajectory is formed in this example by a series of jumps performed between 2 successive images by around fifteen nanoparticles, each of them identified in FIG. 7 by a symbol shown in the legend.

Starting from these experimental measurements, it is possible (as previously) to determine the scattered light amplitude (a value denoted in arbitrary units opposite each symbol in the legend). Here, the scattered amplitude is substantially identical for all the nanoparticles and one may infer the presence of a homogeneous population of virus of "phage T4" type with diameter of 90 nanometers.

Analysis of the trajectories makes it possible to provide supplemental information to the measured values of the scattered strength. In fact, analysis of the Brownian movement also makes it possible to deduce specific information about the nanoparticles, for example, their dimensions, the presence of a tail perturbing the Brownian movement, etc.

Although described through a certain number of sample embodiments, the optical method for detection of nanoparticles in a fluid environment according to the invention and the device for implementing said method have different variants, modifications and improvements which will be obvious to the skilled person, it being understood that these different variants, modifications and improvements are part of the scope of the invention as defined by the following claims.

The invention claimed is:

1. A device for optically detecting in transmission nanoparticles moving in a fluid sample, comprising:
   a light source for emitting a spatially incoherent beam for illuminating the sample;
   an imaging optical system comprising a microscope objective that collects beams scattered by each of the nanoparticles and the incoherent beam passed through the sample in transmission;
   a two-dimensional optical detector comprising a detection plane conjugated with an object focal plane of the microscope objective by said imaging optical system, and allowing a sequence of images of an analysis volume of the sample to be acquired, each image resulting from optical interferences between the incoherent beam passed through the sample and the beams scattered by each of the nanoparticles present in the analysis volume during a preset duration shorter than one millisecond; and
   a processor that averages a sequence of said images to be taken and said average to be subtracted from each image in order to determine, for each nanoparticle of the analysis volume, the amplitude of the scattered beam.

2. The device according to claim 1, wherein the light source is a pulsed source, enabling sequential emitting of light pulses of said preset duration, and the processor synchronizes the two-dimensional optical detector and the pulsed light source for the acquisition of said sequence of images.

3. The device according to claim 1, wherein the microscope objective used has a numerical aperture greater than or equal to 1.

4. A method for optically detecting in transmission nanoparticles moving in a fluid sample, comprising:
   emitting a spatially incoherent light beam for illuminating the sample;
   using an imaging optical system comprising a microscope objective, that collects beams scattered by each of the nanoparticles and the incoherent beam passed through the sample in transmission, to form, on a detection plane of a two-dimensional optical detector, images of an analysis volume of the sample located in the vicinity of an object focal plane of the microscope objective;
   acquiring, from the two-dimensional detector, a sequence of images of the analysis volume of the sample, each image resulting from optical interferences between the incoherent beam passed through the sample and the beams scattered by each of the nanoparticles present in the analysis volume during a preset duration shorter than one millisecond; and
   processing the images to take an average of a sequence of said images and subtract said average from each image in order to determine, for each nanoparticle of the analysis volume, the amplitude of the scattered beam.

5. The method according to claim 4, wherein:
   emitting the light beam comprises sequentially emitting light pulses of said preset duration; and
   acquiring the images is synchronized with the emission of the light pulses.

6. The method according to claim 4, further comprising:
   determining trajectories of the nanoparticles starting from the sequence of processed images.

7. The device according to claim 2, wherein the microscope objective used has a numerical aperture greater than or equal to 1.

8. The method according to claim 5, further comprising:
   determining trajectories of the nanoparticles starting from the sequence of processed images.

\* \* \* \* \*